United States Patent
Wang et al.

(10) Patent No.: US 9,928,609 B2
(45) Date of Patent: Mar. 27, 2018

(54) MEDICAL IMAGE PROCESSING APPARATUS AND MEDICAL IMAGE PROCESSING METHOD

(71) Applicant: Toshiba Medical Systems Corporation, Otawara-shi (JP)

(72) Inventors: Yanli Wang, Beijing (CN); Costas Plakas, Edinburgh (GB); Yanhua Wang, Beijing (CN); Shaobin Wang, Beijing (CN); Minfeng Xu, Beijing (CN); Jianchun Zhao, Beijing (CN); Qi Chen, Beijing (CN); Marco Razeto, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 204 days.

(21) Appl. No.: 15/066,247

(22) Filed: Mar. 10, 2016

(65) Prior Publication Data
US 2016/0267654 A1 Sep. 15, 2016

(30) Foreign Application Priority Data

Mar. 10, 2015 (CN) .......................... 2015 1 0104418
Nov. 30, 2015 (JP) ................................ 2015-234014

(51) Int. Cl.
 *G06T 7/00* (2017.01)
 *G06T 7/30* (2017.01)
 (Continued)

(52) U.S. Cl.
 CPC ............... *G06T 7/30* (2017.01); *A61B 6/032* (2013.01); *G06T 7/0012* (2013.01); *G06T 7/20* (2013.01);
 (Continued)

(58) Field of Classification Search
None
See application file for complete search history.

(56) References Cited

U.S. PATENT DOCUMENTS 8,553,955 B2 * 10/2013 Arakita ................. A61B 6/032
 382/107
2009/0022379 A1 * 1/2009 Tashiro ................. A61B 6/466
 382/131

(Continued)

FOREIGN PATENT DOCUMENTS

JP 2014-108208 6/2014

*Primary Examiner* — Utpal Shah
(74) *Attorney, Agent, or Firm* — Oblon, McClelland, Maier & Neustadt, L.L.P.

(57) ABSTRACT

A medical image processing apparatus according to one embodiment includes obtaining circuitry, calculating circuitry, and transforming circuitry. The obtaining circuitry takes an expiration time phase or an inspiration time phase as a benchmark time phase and obtains a benchmark line structure, which is a line structure of a bronchus in a lung field, from a medical image at the benchmark time phase. The calculating circuitry calculates a motion amount between a component depicted in the medical image at the benchmark time phase and a component depicted in a medical image at at least one other time phase than the benchmark time phase. The transforming circuitry transforms the benchmark line structure based on the motion amount to obtain an estimated line structure, which is estimated as a line structure at the at least one other time phase.

18 Claims, 13 Drawing Sheets

(51) Int. Cl.
  *A61B 6/03* (2006.01)
  *G06T 7/20* (2017.01)
(52) U.S. Cl.
  CPC ............... *G06T 2207/30061* (2013.01); *G06T 2207/30172* (2013.01)

(56) References Cited

U.S. PATENT DOCUMENTS

| | | | |
|---|---|---|---|
| 2011/0243401 A1* | 10/2011 | Zabair | G06K 9/00 382/128 |
| 2015/0257655 A1 | 9/2015 | Ishii et al. | |
| 2016/0022240 A1* | 1/2016 | Yamagata | A61B 6/5217 382/131 |
| 2016/0203609 A1* | 7/2016 | Wang | A61B 5/055 382/131 |

* cited by examiner

A PAIR OF MASKS BEFORE BEING MERGED

NEW MASK GENERATED AFTER MERGING TWO MASKS

CENTRAL LINE TREE WITH A MATCHING LABEL AT AN
INSPIRATION TIME PHASE

MATCHING PRECISION: 80%

CENTRAL LINE TREE WITH A MATCHING LABEL AT AN EXPIRATION TIME PHASE
(LOCAL RIGID REGISTRATION NOT BEEN PROCEEDED)

MATCHING PRECISION: 80%

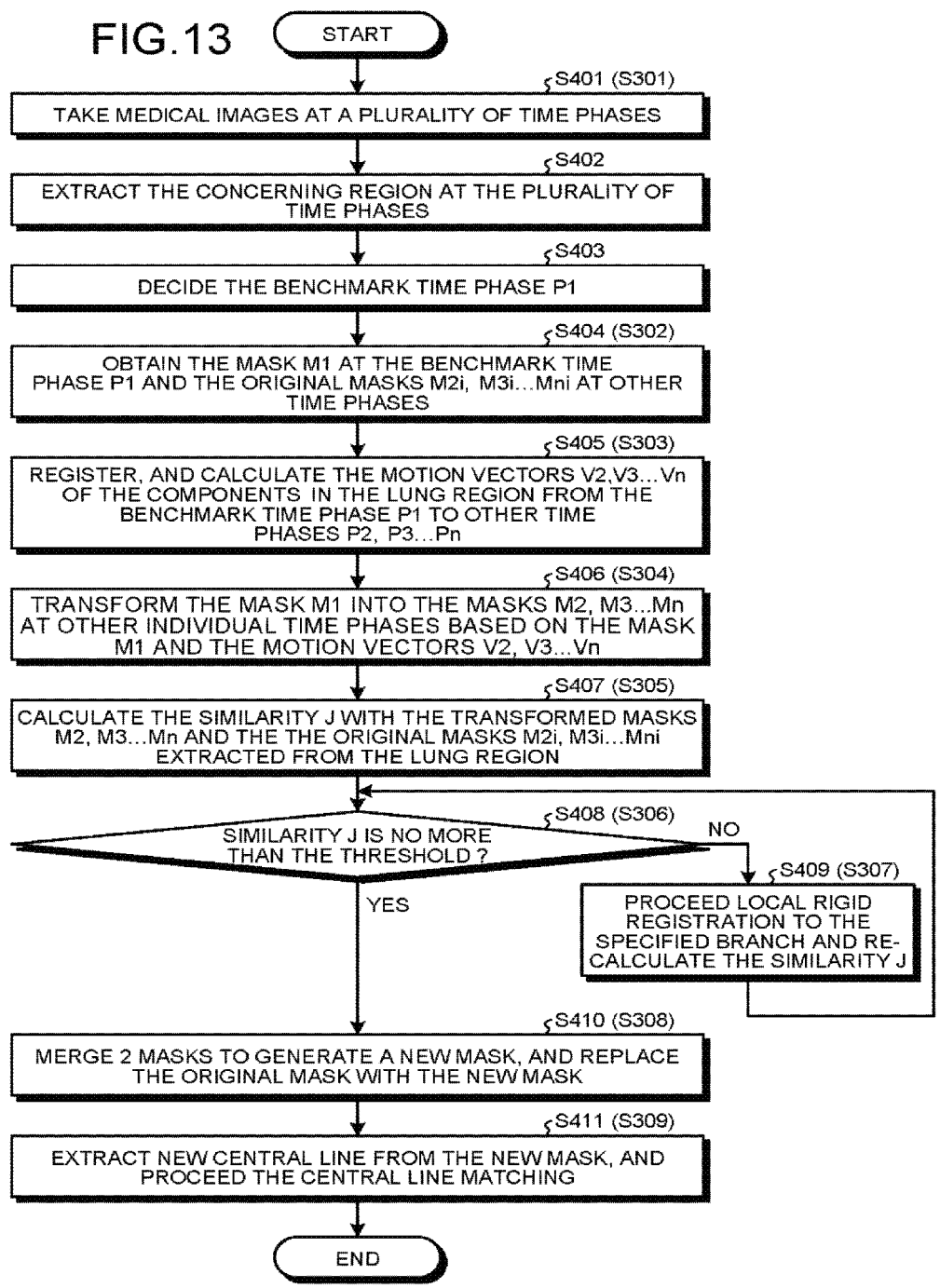

MEDICAL IMAGE PROCESSING APPARATUS AND MEDICAL IMAGE PROCESSING METHOD

CROSS-REFERENCE TO RELATED APPLICATIONS

This application is based upon and claims the benefit of priority from Chinese Patent Application No. 201510104418.1, filed on Mar. 10, 2015; and Japanese Patent Application No. 2015-234014, filed on Nov. 30, 2015, the entire contents of which are incorporated herein by reference.

FIELD

Embodiments described herein relate to a medical image processing apparatus and a medical image processing method.

BACKGROUND

In recent years, in order to make a disease and symptom analysis of chronic obstructive pulmonary diseases (COPD), emphysema, and trachea and bronchus diseases, it is required to have a positional registration on the images of a plurality of tree-like constructions obtained at different time phases of three-dimensional (3D) trachea and bronchus images. However, as respiration is a process of dynamic movement, there will be errors in data processing and analysis due to the dynamic movement.

Japanese Patent Publication No. 2014-108208 discloses an image processing method for heart, by which the processing time and the analytical error based on heartbeats can be reduced. In this technical solution, medical images of the heart region at a plurality of time phases are extracted, and, based on the medical images of the heart region at the plurality of time phases, medical images of the heart region at other time phases are interpolated. Accordingly, there is no need to take the medical images at all time phases as has been done previously, resulting in reduced time for shooting and data processing. Moreover, calculating a central line structure of an artery at other time phases by selecting the time phase, where the heart has almost no movement, as a benchmark time phase removes the errors appearing in the images due to the heart movement.

However, in Japanese Patent Publication No. 2014-108208, the selected cardiac regions at the plurality of time phases, where the heart has almost no movement, includes the cardiac region where the heart is in the end-systolic period; when the cardiac region in the end systolic period is selected, while the extraction of the central line of the artery is hardly influenced, the detection precision thereof becomes lower for the extraction of the central line of tiny vessels, such as capillary vessels, since the capillary vessels in the end-systolic period become finer than the capillary vessels in other periods. As a result, in the case of calculating the cardiac region at other time phases based on the heart region in the end-systolic period, there is likely to be a phenomenon that the vein of capillary vessels is lost. That is, the image processing method in Japanese Patent Publication No. 2014-108208 does not apply to the extraction of tiny tubular structures.

In the observation of the lung region, the operator sometimes desires to merely observe the morphologies of the trachea itself at individual time phases. However, in previous techniques, the images of the trachea extracted during the respiratory cycle, besides containing its own variations, further contains the positional movement brought about by the lung movement. That is, in previous techniques, the 3D images of the lung region at individual time phases are obtained by taking images of this region, and then the central lines of the tree-like structure (i.e. trachea and bronchus) at individual time phases are extracted based on the obtained 3D images. With previous techniques, however, the changes of the airway position caused by the contraction and expansion of the lung are mixed together with the changes of the contraction and expansion of the airway itself in respiratory movements, and the actual amount of change of the airway contains not only the motion amount of itself but also the changes in position produced as the lung moves; thus there is a situation where the states of change of the airway itself cannot be precisely reflected when directly extracting the airway at individual time phases. Thus, it is desirable to remove the change in position of the airway due to the contraction and expansion of the lung.

Moreover, in the observation of the lung region, the operator sometimes desires to extract the tinier tube portions, such as the end of the bronchus and so on; however, with the solution of prior art, it is unable to precisely extract the tiny tube portions. Thus, an approach that can precisely extract the entire tube portion is desirable. More specifically, it is desirable to be able to precisely detect the changes in spatial position of the airway itself at individual time phases and to completely reproduce the entire airway including the tiny pipeline ends.

Embodiments described herein are intended to provide a medical image processing apparatus and a medical image processing method that can precisely reproduce the line structures of the bronchus at individual time phases.

The medical image processing apparatus of the embodiments includes obtaining circuitry, calculating circuitry, and transforming circuitry. The obtaining circuitry takes an expiration time phase or an inspiration time phase as a benchmark time phase, and obtains a benchmark line structure, which is a line structure of the bronchus in the lung field, from a medical image at the benchmark time phase. The calculating circuitry calculates a motion amount between a component depicted in the medical image at the benchmark time phase and the component depicted in the medical image at at least one other time phase than the benchmark time phase. The transforming circuitry transforms the benchmark line structure based on the motion amount to obtain an estimated line structure, which is estimated as a line structure at the at least one other time phase.

BRIEF DESCRIPTION OF THE DRAWINGS

FIG. 13 is a flowchart representing the processing procedure of the medical image processing apparatus of embodiment 4.

DETAILED DESCRIPTION

A medical image processing apparatuses and a medical image processing methods according to embodiments are described below in detail in connection with the drawings. Note that embodiments are not limited to the embodiments described below. In principle, descriptions regarding one embodiment similarly apply also to the other embodiments.

A medical image processing apparatus according to one embodiment includes obtaining circuitry, calculating circuitry, and transforming circuitry. The obtaining circuitry takes an expiration time phase or an inspiration time phase as a benchmark time phase and obtains a benchmark line structure, which is a line structure of a bronchus in a lung field, from a medical image at the benchmark time phase. The calculating circuitry calculates a motion amount between a component depicted in the medical image at the benchmark time phase and a component depicted in a medical image at at least one other time phase than the benchmark time phase. The transforming circuitry transforms the benchmark line structure based on the motion amount to obtain an estimated line structure, which is estimated as a line structure at the at least one other time phase.

In the following embodiments, detailed descriptions are made taking the trachea and bronchus in the lung region (also called the lung field) as example. Here, the lung region may be a part of the lung. Note that processing to be executed by the medical image processing apparatuses and the medical image processing methods according to embodiments is not limited to processing on the tree-like composition of the trachea and bronchus, and is also applicable to processing on the images of other tree-like structures of, for example, cranial nerves and vessels, besides the trachea and bronchus.

Embodiment 1

Figure 1:
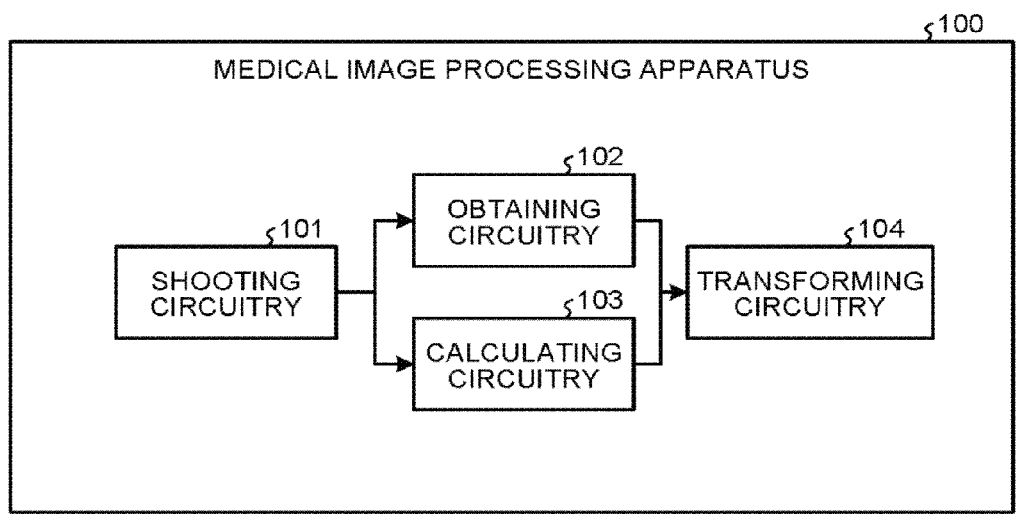
FIG. 1 is a block diagram representing a medical image processing apparatus of embodiment 1.

FIG. 1 is a block diagram representing a medical image processing apparatus of embodiment 1.

As shown in FIG. 1, a medical image processing apparatus 100 comprises shooting circuitry 101, obtaining circuitry 102, calculating circuitry 103 and transforming circuitry 104.

The shooting circuitry 101 takes images of a subject used as an examining object, getting a plurality of medical images of the subject on the time sequence. Here, the medical images are three-dimensional (3D) medical images. Taking one respiratory cycle as example, the plurality of medical images are those taken in terms of every time phase during the period from the start of the inspiration stage to the end of the expiration stage. The medical images comprise the region of interest by the operator as a concerning region. The concerning region in the present embodiment is, but not limited to, the lung region.

The obtaining circuitry 102 takes an expiration time phase or an inspiration time phase as the benchmark time phase and obtains a benchmark line structure, which is a line structure of the bronchus in the lung field from a medical image at the benchmark time phase. Here, the obtaining circuitry 102 takes the reference line of the bronchus in the lung field as the line structure. For example, the obtaining circuitry 102 takes a time phase on the time sequence as the benchmark time phase P1, obtaining the central line C1 of the trachea and bronchus of tree-like line structure from the lung region at the benchmark time phase P1 as the benchmark line structure, but the line structure of the present embodiment is not limited to the central line. The method of obtaining the central line is not limited either, and can be any method of the prior arts.

The calculating circuitry 103 calculates motion amounts between elements depicted in the medical image at the benchmark time phase and the elements depicted in each of the medical images at time phases (also referred to as target phases) other than the benchmark time phase. For example, the calculating circuitry 103 registers the components in the lung region at the benchmark time phase P1 and the components in the lung region at other individual time phases (P2, P3, . . . , Pn) used as the target time phases, calculating the motion vectors (V2, V3, . . . , Vn) of the components in the lung region from the benchmark time phase P1 to other individual time phases (P2, P3, . . . , Pn), respectively. In other words, the calculating circuitry 103 calculates the motion amount by performing a registration between the medical image at the benchmark time phase and each of the medical images at other time phases.

The transforming circuitry 104 obtains estimated line structures, which are estimated as line structures at other time phases by transforming the benchmark line structure based on the motion amounts. For example, based on the motion vectors (V2, V3, . . . , Vn) from the benchmark time phase P1 to other individual time phases (P2, P3, . . . , Pn) calculated by the calculating circuitry 103 and the central line C1 of the airway of the lung region at the benchmark time phase P1 obtained by the obtaining circuitry 102, the transforming circuitry 104 transforms the central line C1 of the airway at the benchmark time phase P1 into the central lines (C2, C3, . . . , Cn) of the airway at other individual time phases (P2, P3, . . . , Pn) used as the target time phases, respectively.

Figure 2:
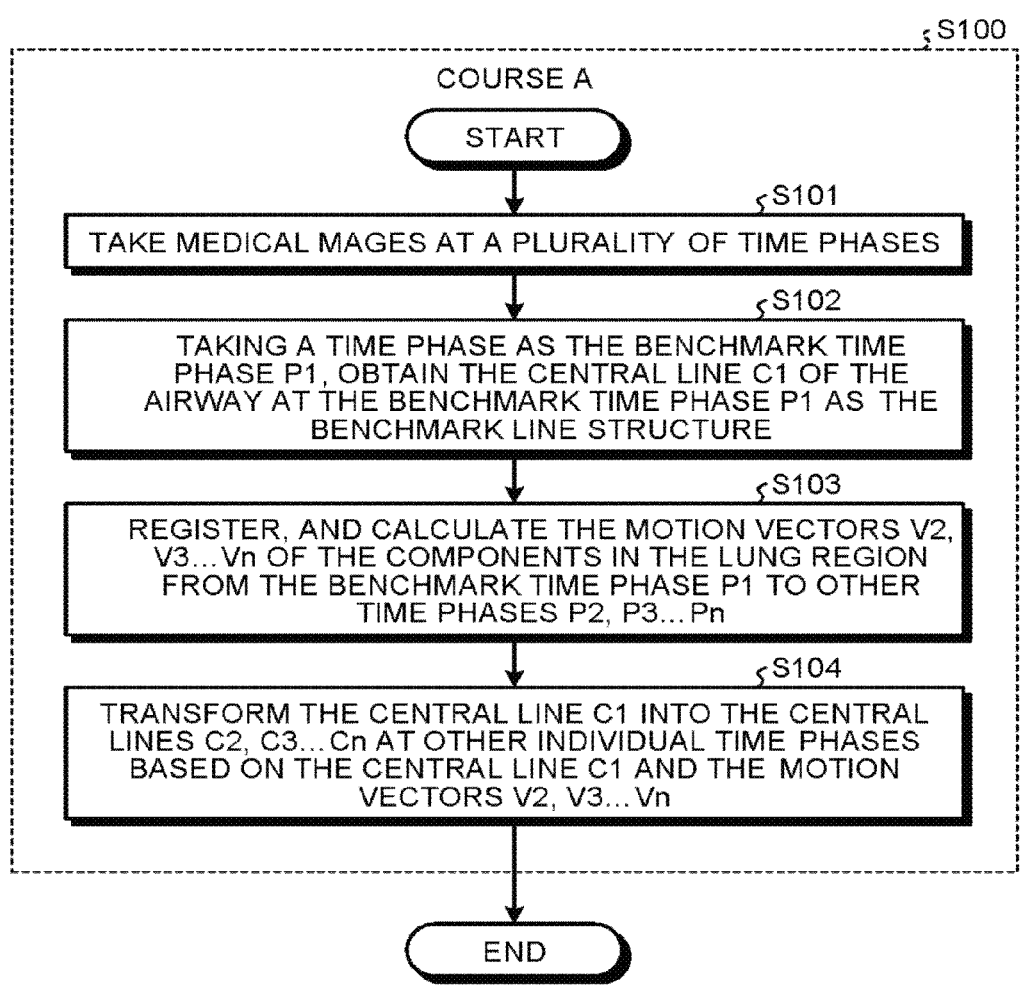
FIG. 2 is a flowchart representing the processing procedures of the medical image processing apparatus of embodiment.

Then the processing procedure of the medical image processing apparatus 100 of the present embodiment is illustrated in the following. FIG. 2 is a flowchart representing the processing procedure of the medical image processing apparatus of embodiment 1.

The medical image processing apparatus 100 takes medical images of the subject at a plurality of time phases by the shooting circuitry 101 (step S101). In t; the medical images include the sites concerned by the observer, i.e. the concerning region, which in the present embodiment is, but not limited to, the lung region.

In step S102, the obtaining circuitry 102, taking a time phase on the time sequence as the benchmark time phase, obtains the central line C1 of the airway at the benchmark time phase P1 from the lung region at the benchmark time phase P1. The method of obtaining the central line C1 is not specifically limited, and can be any method of the prior arts.

In step S103, the calculating circuitry 103 respectively registers the components in the lung region at the benchmark time phase P1 and the components in the lung region at other individual time phases (P2, P3, . . . , Pn), calculating the motion vectors (V2, V3, . . . , Vn) of the components in the lung region from the benchmark time phase P1 to other individual time phases (P2, P3, . . . , Pn). For example, taking the calculation on motion vector V2 as example, the calculating circuitry 103 registers the components in the lung region at the benchmark time phase P1 and the components in the lung region at the time phase P2, calculating the motion vector V2 of the components in the lung region from the time phase P1 to the time phase P2. Likewise, the calculating circuitry 103 further calculates the motion vectors V3, V4, etc.

Moreover, the above mentioned registration preferably uses non-rigid registration, the registration method thereof is not specifically defined, and other registration methods in the prior arts can also be employed.

There is no particular execution order between the above mentioned steps S102 and S103. Either of the steps S102 and S103 can be carried out first, and the steps S102 and S103 can also be carried out simultaneously.

In step S104, the transforming circuitry 104 transforms the central line C1 respectively with the central line C1 of the airway at the benchmark time phase P1 obtained by the obtaining circuitry 102 in step S102 and the motion vectors (V2, V3, . . . , Vn) of the components in the lung region from the benchmark time phase P1 to other individual time phases (P2, P3, . . . , Pn) calculated by the calculating circuitry 103 in step S103, getting the central lines (C2, C3, . . . , Cn) of the airway at other individual time phases. In other words, the transforming circuitry 104 transforms the benchmark line structure into the estimated line structures by assigning corresponding motion amounts to the benchmark line structure.

The transformed central lines (C2, C3, . . . , Cn) resulting from the above processing are the central lines which have the positional movement produced as the movement of the lung region removed and only represent the movement of the airway itself.

Figure 3:
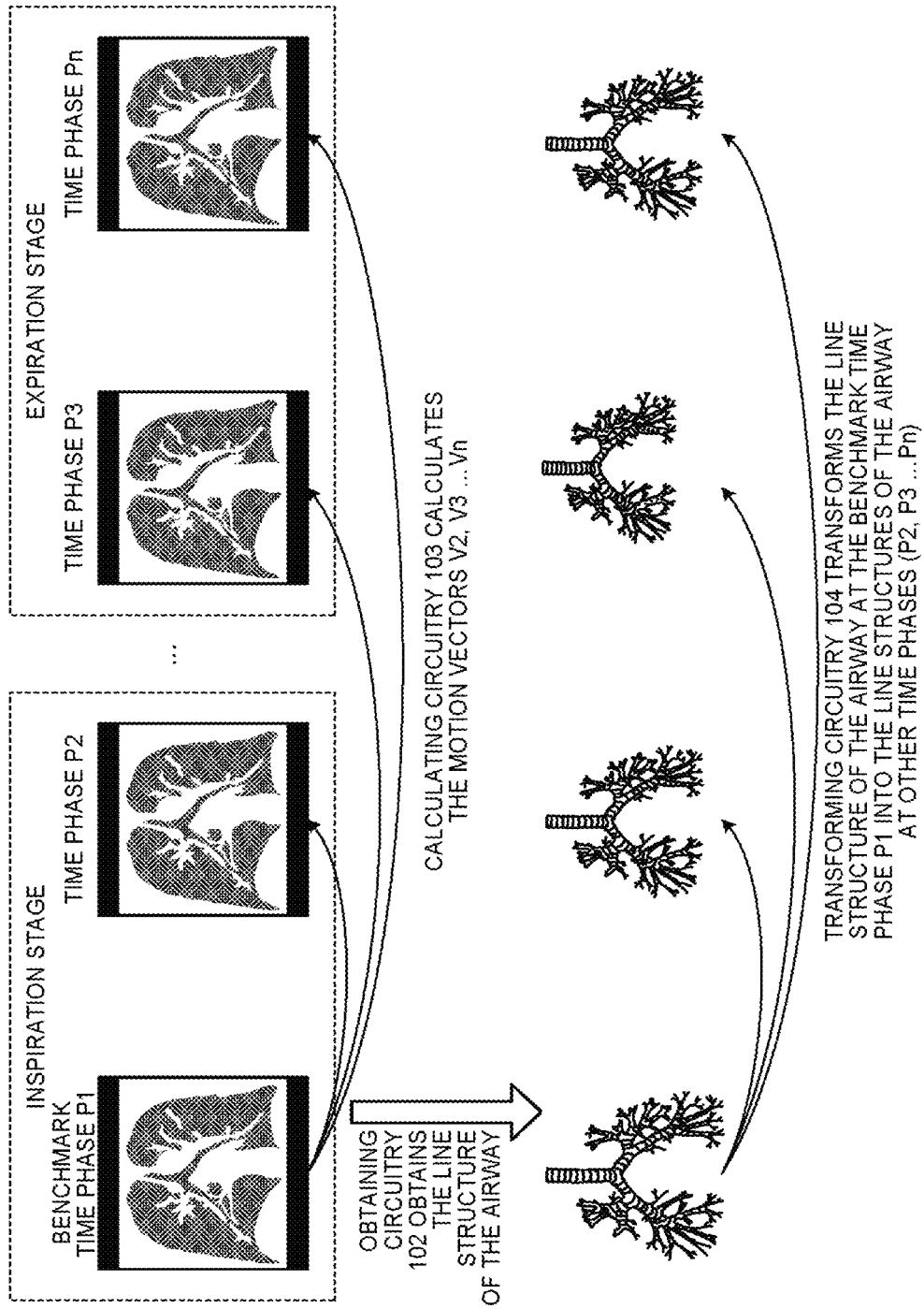
FIG. 3 is a schematic diagram representing the actions of the obtaining circuitry, the calculating circuitry and the transforming circuitry of embodiment 1.

FIG. 3 is a schematic diagram representing the actions of the obtaining circuitry, the calculating circuitry and the transforming circuitry of the embodiment 1. As shown in FIG. 3, the medical images of the subject at a plurality of time phases are taken by the shooting circuitry, the 2 images on the left of FIG. 3 are the images taken in the inspiration stage, and the 2 images on the right are the images taken in the expiration stage; taking time phase when the left-most medical image is taken as the benchmark time phase, the central line of the airway (FIG. 3 only shows the tube portion model but omits the illustration of the central line) is obtained as the benchmark line structure from the lung region at this time phase with the obtaining circuitry 102, and the components in the lung region at this time phase and the components in the lung region at the 3 time phases on the right are obtained by the calculating circuitry 103; the motion vectors of the components in the lung region from the left-most time phase to the 3 time phases on the right are calculated respectively; based on the motion vector from the left-most time phase to the 3 time phases on the right calculated by the calculating circuitry 103 and the central line of the airway at the left-most time phase obtained by the obtaining circuitry 102, the central lines at the left-most time phase are respectively transformed by the transforming circuitry 104 into the central lines at the 3 time phases on the right used as the target time phases.

According to the above processing course, the present embodiment does not use the central lines of the airway extracted directly from the lung region used as the concerning region at the target time phase, instead, the central lines of the airway at the target time phase resulting from the transformation on the central lines of the airway at the benchmark time phase are used so as to remove the changes in position of the airway due to the movement of the lung region. Thereby, the errors caused by the changes in position of the airway can be eliminated, only the changes of the airway itself are concerned, and medical images with higher precision are obtained.

Moreover, the steps from the "start" in FIG. 2 to S104 are referred as a "course A".

As described above, according to embodiment 1, the changes in position of the airway due to the contraction and expansion of the lung can be removed, which enables precisely detection of the changes of the airway itself, and completely reproduction of the entire airway including the ends of tiny tubes at individual time phases.

Variation of Embodiment 1

In the variation of the embodiment 1, after step S104, the transformed central lines (C2, C3, . . . , Cn) are further repositioned to the center of the airway by the transforming circuitry 104 and are smoothed. More specifically, with the positions of prescribed key points on the estimated line structures maintained based on the medical images at other time phases, the transforming circuitry 104 repositions the central line of the branches in each of the estimated line structure to the center of the bronchus. With the positions of key points on the estimated line structure maintained, the transforming circuitry 104 then smoothes the branches in the estimated line structure.

Figure 4:
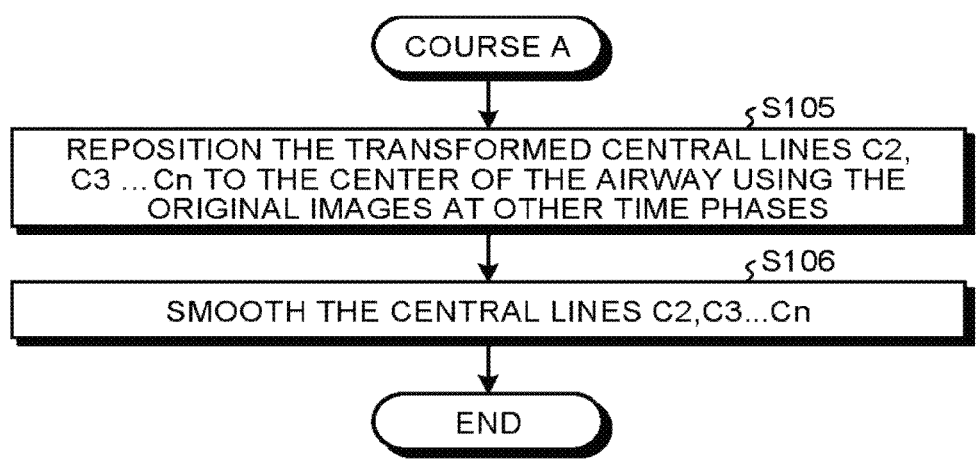
FIG. 4 is a flowchart representing the processing procedure of a variation of embodiment 1.

FIG. 4 is a flowchart representing the processing procedure of the variation of embodiment 1.

After the "course A", step S105 is performed in FIG. 4. In step S105, using the images of the lung region at other individual time phases (P2, P3, . . . , Pn), the points on the connecting lines between the key points are all repositioned to the center of the airway with the positions of prescribed key points on the central line maintained.

Figure 5A:
FIG. 5A is a schematic diagram representing the positions of the central line before and after a repositioning in a variation of embodiment 1.
Figure 5B:
FIG. 5B is a schematic diagram representing the positions of the central line before and after a repositioning in the variation of embodiment 1.

FIG. 5A and FIG. 5B are schematic diagrams representing the positions of the central line before and after a repositioning of center of a variation of embodiment 1. As shown in FIG. 5A and FIG. 5B, the transformed central lines are combined with the images of the lung region at the corresponding time phase, as shown in FIG. 5A; at the moment, the points on the transformed central lines are not always at the center of the airway, but may have deviation. Now with the positions of the prescribed key points maintained on the central line, the prescribed points on the connecting lines between the key points are repositioned. When repositioned, every prescribed point on the connecting lines is sliced up once in the direction of the width of the airway, and the prescribed points on the connecting lines can be respectively positioned to the central positions of the airway on the airway sliced image in a slice by slice order using the snake algorithm. Therefore the prescribed points on the connecting lines between the key points are repositioned to the center of the airway, so as that the entire central line is in the state after the repositioning of center as shown in FIG. 5B. The method of repositioning the central line is not limited thereto, and other methods can also be used as long as they can have the central line repositioned to the center of the airway.

In step S106, using the images of the lung region at other individual time phases (P2, P3, ..., Pn), all the branches of the transformed central line C2, C3, ..., Cn are smoothed with the positions of the prescribed key points on the central line being maintained. For example, the length of the central line C2 is calculated first; then the prescribed point pitch is set; with the positions of the prescribed key points on the central line C2 maintained, new points are generated in terms of the prescribed point pitch, to replace the points on the original central line, so as to implement the smoothing of the central line. But the method of smoothing is not limited thereto, and other methods can also be used as long as they can have the smoothing of the central line of the airway implemented.

The order between the above steps S105 and S106 is not defined. Although in the present embodiment, the repositioning of the central line is performed first and followed by the smoothing, the smoothing can also be performed first and followed by the repositioning of the central line.

Embodiment 2

Figure 6:
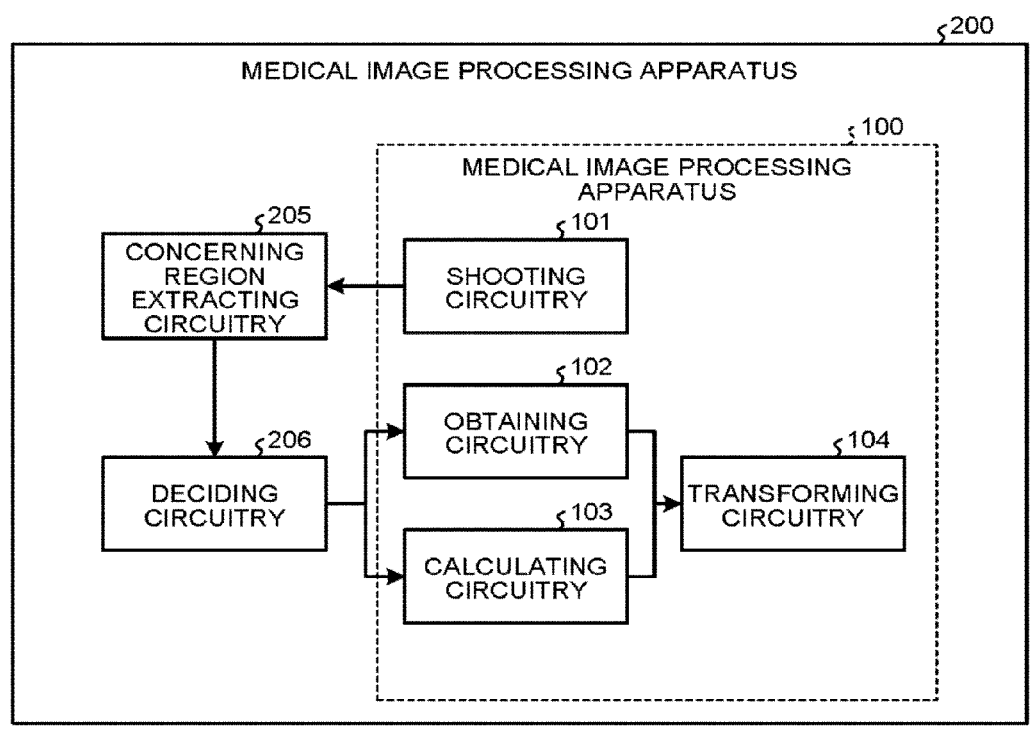
FIG. 6 is a block diagram representing a medical image processing apparatus of embodiment 2.

FIG. 6 is a block diagram representing the medical image processing apparatus of embodiment 2. As shown in FIG. 6, besides the shooting circuitry 101, the obtaining circuitry 102, the calculating circuitry 103, and the transforming circuitry 104 in the medical image processing apparatus 100, a medical image processing apparatus 200 in embodiment 2 further comprises: concerning region extracting circuitry 205 and deciding circuitry 206, wherein the concerning region extracting circuitry 205 is not essential and can be omitted. The element with like reference numbers represents the same as that in embodiment 1. Only the differences are illustrated below, with the description on the same parts omitted.

The concerning region extracting circuitry 205 extracts a concerning region from a medical image. For example, the concerning region extracting circuitry 205 extracts the region of interest by the observer (e.g. the lung region) from the components in the medical images taken by the shooting circuitry 101, and takes the extracted region as the concerning region. The concerning region can be the prescribed region both specified by the operator manually and gained based on the calculation of a computer.

The deciding circuitry 206 decides one time phase from the plurality of time phases on the time sequence for shooting the subject as the benchmark time phase. In accordance with the benchmark time phase P1 decided by the deciding circuitry 206, the obtaining circuitry 102 obtains the central line C1 of the trachea and bronchus of the tree-like line structure from the lung region at the benchmark time phase P1 as the benchmark line structure, to perform the subsequent transformation from the central line C1 of the airway at the benchmark time phase P1 to the central line (C2, C3, ..., Cn) of the airway at other individual time phases (P2, P3, ..., Pn).

The deciding method of the benchmark time phase will be described. Based on the concerning region depicted in the medical images, the deciding circuitry 206 decides a medical image at the benchmark time phase. Here, the deciding circuitry 206 may decide it based on the dimension of the extracted concerning region. For example, based on the dimension of the lung field depicted in the medical image, the deciding circuitry 206 may decide the medical image at the benchmark time phase. Alternatively, the deciding circuitry 206 may decide it based on the pixel values of the concerning region. For example, based on the pixel values of the lung field depicted in the medical image, the deciding circuitry 206 may decide the medical image at the benchmark time phase. Here, the deciding circuitry 206 uses the correlation between the dimension of the lung field and the CT value. More specifically, the CT value is larger as the lung field is larger. Alternatively, the deciding circuitry 206 may calculate the mean density of the concerning region in accordance with the pixel values of the concerning region first and then decide the benchmark time phase according to the calculated mean density. More specifically, the deciding circuitry 206 calculates the mean lung density based on the pixel values, thereby deciding the medical image at the benchmark time phase. In the embodiment, the time phase used as the benchmark time phase can be decided based on the dimension of the lung region; the time phase used as the benchmark time phase can also be decided based on the pixel values of the lung region; it is also operable to calculate the mean density of the lung in accordance with the pixel values of the lung region first, then decide the benchmark time phase in accordance with the calculated mean density of the lung.

Figure 7:
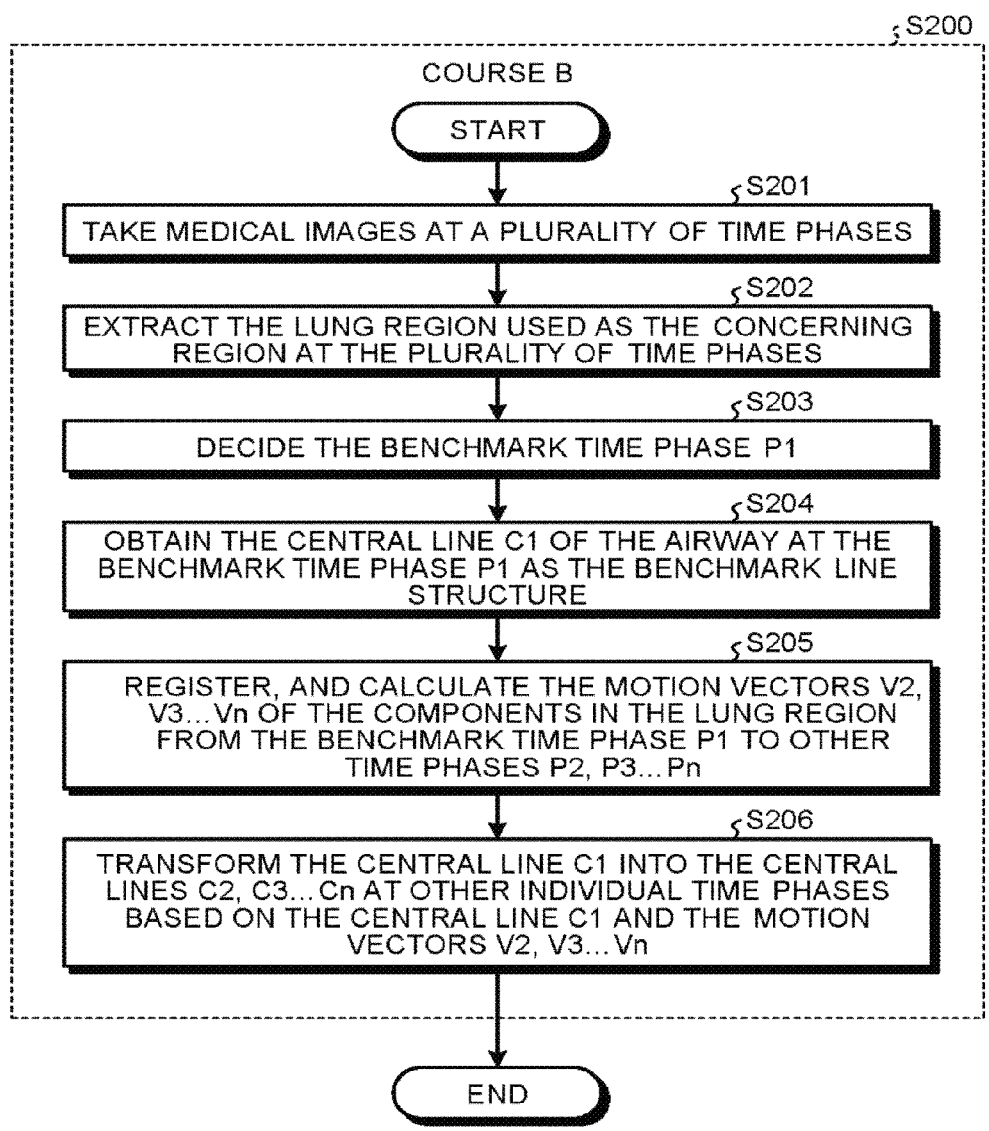
FIG. 7 is a flowchart representing the processing procedure of the medical image processing apparatus of embodiment 2.

The processing procedure of the medical image processing apparatus 200 of the present embodiment then is illustrated in the following. FIG. 7 is a flowchart representing the processing procedure of the medical image processing apparatus of embodiment 2.

The medical image processing apparatus 200 takes medical images of a subject at a plurality of time phases by shooting circuitry 201 (step S201), the medical images include the sites concerned by the observer, i.e., the concerning region, which in the present embodiment is, but not limited to, the lung region. Then the concerning region extracting circuitry 205 extracts the lung region used as the concerning region from the medical images (step S202). Then the deciding circuitry 206 decides the benchmark time phase P1 based on the parameters of the lung region (step S203), the parameters of the lung region mentioned herein refer to at least one of the dimension of the lung region, the pixel values of the lung region and the mean density of the lung region.

In the present embodiment, the maximal inspiration time phase or the maximal expiration time phase is decided as the benchmark time phase. The maximal inspiration time phase is the time phase in the inspiration stage where the trachea width is maximal; and the maximal expiration time phase is the time phase in the expiration stage where the trachea width is maximal.

In the following, the reason for deciding the maximal inspiration time phase or the maximal expiration time phase as the benchmark time phase will be described. More specifically, the deciding circuitry 206 takes the maximal expiration time phase or the maximal inspiration time phase as the benchmark time phase to decide a medical image at the benchmark time phase. While the maximal expiration time phase indicates a time phase when the lung has the smallest dimension, the maximal inspiration time phase indicates a time phase when the lung has the largest dimension.

For example, in the end of the expiration stage (time phase), due to the contraction of the lung, it is difficult for some tiny local regions of the airway to be completely extracted, thus it is not expected to extract the central line of the airway at this time phase directly. In contrast, at the time phase with maximal airway width, such as the maximal inspiration time phase or the maximal expiration time phase, it is the easiest to extraction the central line of the airway. In the present embodiment, in order to obtain the most completed central line of the airway with least missing, it is needed to select the maximal inspiration time phase or the maximal expiration time phase in which even the tiny airway can be extracted at the most extent, and to take this time phase as the benchmark time phase to extract the central line of the airway at this time phase, so as to guarantee the completeness of the central line of the airway at other individual time phases after the transformation.

By deciding the maximal inspiration time phase or the maximal expiration time phase as the benchmark time phase, the present embodiment can have all the branches of the airway including the tiny local regions completely extracted and obtain a more completed observational image with a higher reliability.

Next, in step S204, in accordance with the benchmark time phase P1 decided by the deciding circuitry 206, the obtaining circuitry 102 obtains the central line C1 of the trachea and bronchus of the tree-like line structure from the lung region at the benchmark time phase P1 as the benchmark line structure; and in step S205, the motion vectors (V2, V3, . . . , Vn) of the components in the lung region from the benchmark time phase P1 to other time phases (P2, P3, . . . , Pn) are calculated by registration; in step S206, the central line C1 is transformed into the central lines (C2, C3, . . . , Cn) of the airway at other individual time phases P2, P3, . . . , Pn based on the central line C1 and the motion vectors (V2, V3, . . . , Vn).

The same as the steps S102 and S103 in the embodiment 1, there is no particular execution order between the steps S204 and S205 in embodiment 2. Either of the steps S204 and S205 can be carried out first, and the steps S204 and S205 can also be carried out simultaneously.

Moreover, the step from the "start" in FIG. 7 to S206 is referred as a "course B".

Variation

As the variation of embodiment 2, being the same as the embodiment, after step S206 the transformed central lines (C2, C3, . . . , Cn) can be further repositioned to the center of the airway by the transforming circuitry 104 and smoothed.

That is, after the "course B" in FIG. 7, the repositioning and the smoothing of the central line of the airway are carried out, the repositioning and the smoothing of the central line of the airway are the same as those of the variation of embodiment 1, and the description is omitted herein.

Embodiment 3

Figure 8:
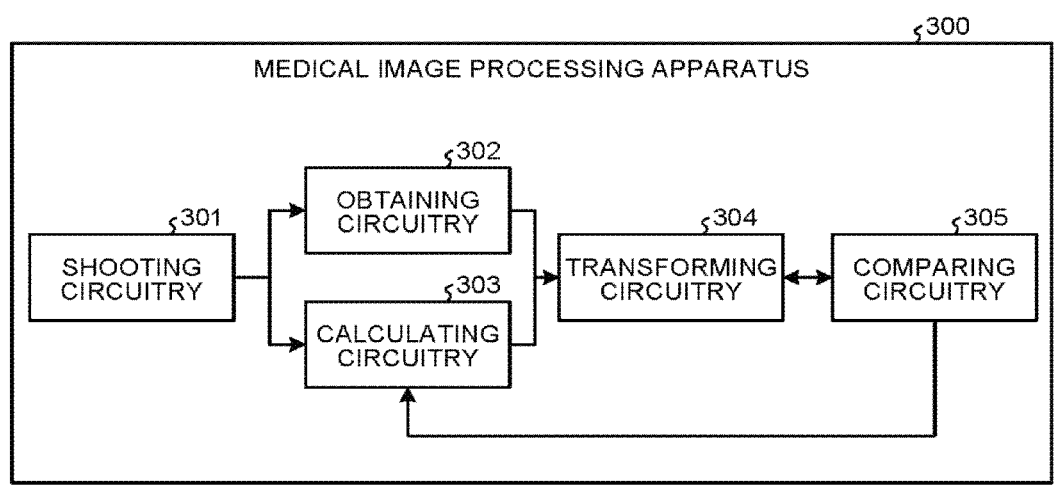
FIG. 8 is a block diagram representing a medical image processing apparatus of embodiment 3.

FIG. 8 is a block diagram representing the medical image processing apparatus of embodiment 3.

As shown in FIG. 8, the embodiment 3 comprises: shooting circuitry 301, obtaining circuitry 302, calculating circuitry 303, transforming circuitry 304, and comparing circuitry 305. Compared with embodiment 1, embodiment 3 has the difference of: the obtaining circuitry 302, the calculating circuitry 303 and the transforming circuitry 304 in embodiment 3 are the variations of the obtaining circuitry 102, the calculating circuitry 103, the transforming circuitry 104 in embodiment 1, and the comparing circuitry 305 is an added circuitry with respect to embodiment 1. Only the different parts are illustrates in the following.

In the embodiment 3, in order to make the precision of the comparison result based on comparing circuitry 207 higher, the image processing is performed using a mask entirely covering the trachea and bronchus as the line structure instead of using the central lines of the trachea and bronchus in embodiment 1. Here, the mask entirely covering the trachea and bronchus indicates a region corresponding to the entirety of the trachea and bronchus. Note that the image processing can also be performed using the central lines of the trachea and bronchus as embodiment 1.

The difference between the obtaining circuitry 302 and the obtaining circuitry 102 is that, the obtaining circuitry 102 obtains only the line structure C1 of the trachea and bronchus at the benchmark time phase P1, while the obtaining circuitry 302 obtains not only the line structure M1 of the trachea and bronchus at the benchmark time phase P1, but also the line structures (M2i, M3i, . . . , Mni) of the trachea and bronchus at other individual time phases (P2, P3, . . . , Pn) as temporary line structures. In other words, in addition to taking an expiration time phase or an inspiration time phase as the benchmark time phase and obtaining the line structure of the bronchus in the lung field from a medical image at that time phase, the obtaining circuitry 302 further obtains the line structures of the bronchus from medical images at other time phases as the temporary line structures. Here, the obtaining circuitry 302 obtains regions corresponding to the bronchus in the lung field as line structures. In other words, the obtaining circuitry 302 obtains masks of the bronchus as line structures.

That is, besides being able to obtain the mask M1 of the trachea and bronchus of the tree-like line structure from the lung region at the benchmark time phase P1 as the benchmark line structure by taking a time phase on the time sequence as the benchmark time phase P1, the obtaining circuitry 302 can further obtain the original masks (M2i, M3i, . . . , Mni) of the trachea and bronchus of the tree-like line structure in the lung region at other individual time phases (P2, P3, . . . , Pn) as the temporary line structure. The temporary line structure refers to the line structure that will change in the subsequent transformation processes.

Besides being able to calculate the motion vectors (V2, V3, . . . , Vn) of the components in the lung region from the benchmark time phase P1 to other individual time phases (P2, P3, . . . , Pn) (like the calculating circuitry 103 of the embodiment 1), the calculating circuitry 303 can further perform a local rigid registration to the specified branch of the bronchus used as the tree if the similarity derived from the comparing circuitry 305 described below is less than the threshold, thereby calculating the motion amounts between the elements on the specified branches of the transformed masks (M2, M3, . . . , Mn) and the elements on the specified branches of the original masks (M2i, M3i, . . . , Mni) extracted directly from the lung region.

Besides being able to transform the mask M1 at the benchmark time phase P1 into the masks (M2, M3, . . . , Mn) at other individual time phases (P2, P3, . . . , Pn) used as the target time phases respectively based on the motion vectors (V2, V3, . . . , Vn) from the benchmark time phase P1 to other individual time phases (P2, P3, . . . , Pn) calculated by the calculating circuitry 303 and the mask M1 of the lung region at the benchmark time phase P1 obtained by the obtaining circuitry 302 (like the transforming circuitry 104 of embodiment 1), the transforming circuitry 304 can further merge the transformed mask with the original masks (M2i, M3i, . . . , Mni) extracted directly from the lung region to generate new masks (M2n, M3n, . . . , Mnn) if the comparison result derived from the comparing circuitry 207 is no less than the threshold, the new masks are taken as the masks at other individual time phases (P2, P3, . . . , Pn).

The comparing circuitry 305 further compares the estimated line structures and the temporary line structures to calculate the similarity. For example, the comparing circuitry 305 compares the transformed masks with the original masks M2i, M3i, . . . , Mni extracted from the lung region, taking the similarity of the both as the comparison result. The calculation of the similarity can be done by the following equation (1).

$$J = \frac{(A \cap B)}{(A \cup B)} \quad (1)$$

A in the above equation is the masks at other individual time phases (P2, P3, . . . , Pn) derived from the transformation, B in the above equation is the original masks (M2i, M3i . . . , Mni) at other individual time phases (P2, P3, . . . , Pn) extracted directly from the lung region, and J is the Jaccard index, i.e. the similarity index.

According to the size relationship between the comparison result J derived from the comparing circuitry 305 and the prescribed threshold, the calculating circuitry 303 and the transforming circuitry 304 carry out different processing. Note that the prescribed threshold may be set to different values for different time phases.

Figure 9:
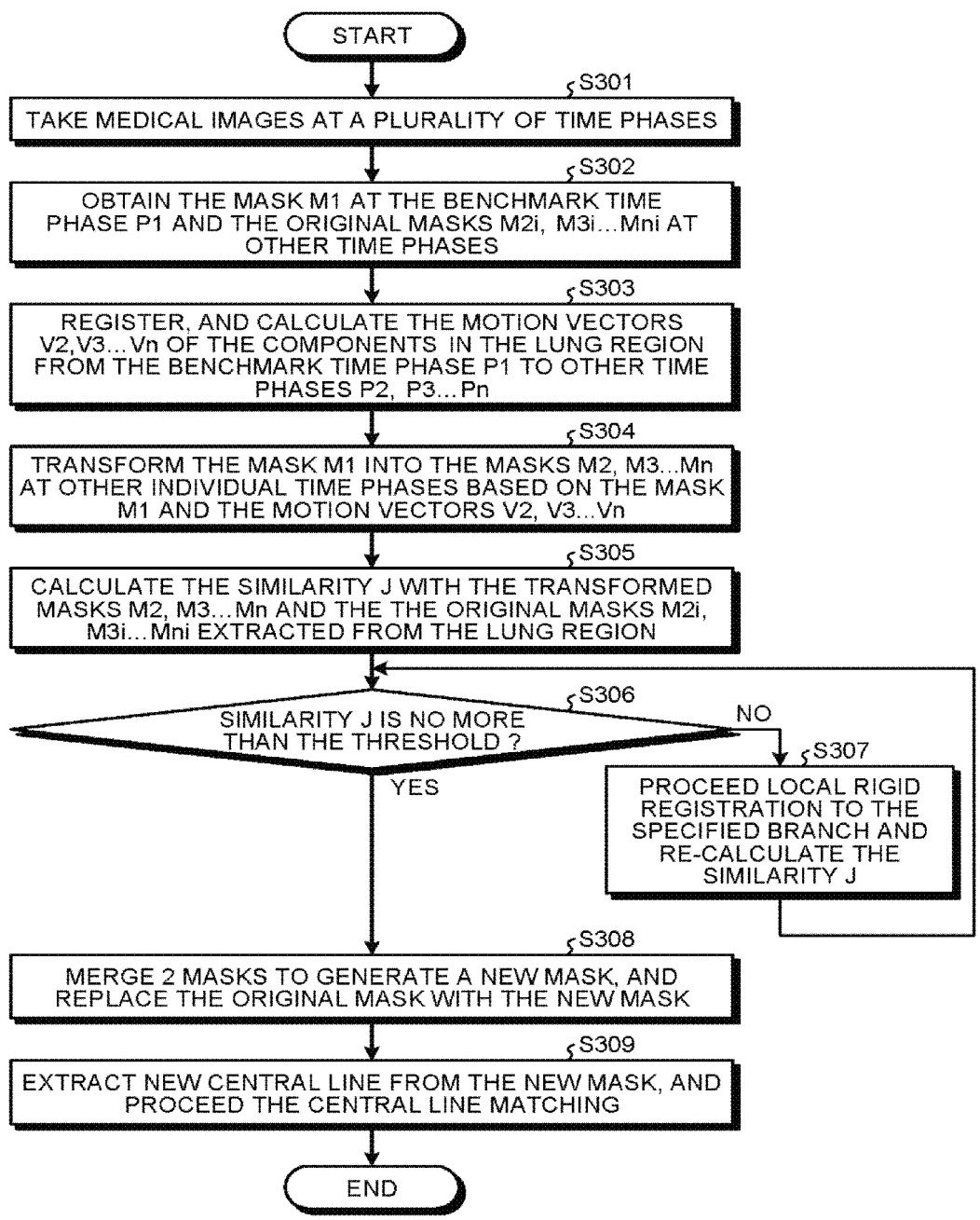
FIG. 9 is a flowchart representing the processing procedure of a medical image processing apparatus of embodiment 3.

The processing procedure of a medical image processing apparatus 300 of the present embodiment is then illustrated in the following. FIG. 9 is a flowchart representing the processing procedure of the medical image processing apparatus of embodiment 3.

In step S301, the shooting circuitry 301 takes medical images of the subject at a plurality of time phases (step S301).

In step S302, taking a time phase on the time sequence as the benchmark time phase P1, the obtaining circuitry 302 obtains the mask M1 of the trachea and bronchus of the tree-like line structure from the lung region at the benchmark time phase P1 as the benchmark line structure, and obtains the original masks (M2i, M3i, . . . , Mni) of the trachea and bronchus of lung region at other individual time phases (P2, P3, . . . , Pn) as the temporary line structures.

In step S303, the calculating circuitry 303 registers the components in the lung region at the benchmark time phase P1 and the components in the lung region at other time phases (P2, P3, . . . , Pn) respectively, calculating the motion vectors (V2, V3, . . . , Vn) of the components in the lung region from the benchmark time phase P1 to other time phases (P2, P3, . . . , Pn).

Moreover, the above mentioned registration preferably uses non-rigid registration, and the registration method thereof is not specifically defined. Registration methods in the prior art can be employed.

There is no particular execution order between the above mentioned steps S302 and S303. Both the steps S302 and S303 can be carried out first, and the steps S302 and S303 can also be carried out simultaneously.

In step S304, the transforming circuitry 304 transforms the mask M1 respectively with the mask M1 at the benchmark time phase P1 obtained by the obtaining circuitry 302 in step S302 and the motion vectors (V2, V3, . . . , Vn) of the components in the lung region from the benchmark time phase P1 to other individual time phases (P2, P3, . . . , Pn) calculated by the calculating circuitry 303 in step S303, getting the transformed masks (M2, M3, . . . , Mn) at other individual time phases. If taking the transformation on the mask M1 at the benchmark time phase P1 into the mask M2 at the time phase P2 as example, the transforming circuitry 304 gives the mask M1 the motion vector V2 corresponding thereto so as to get the transformed mask, which is the transformed mask M2 at the time phase P2.

The transformed masks (M2, M3, . . . , Mn) are the masks with the positional movement of the airway due to the movement of the lung region removed and only representing the movement of the airway itself.

According to the above processing course, the present embodiment removes the changes in position of the airway brought by the movement of the lung region; thus, the influence brought by the errors is eliminated, only the changes of the airway itself are concerned, and the medical images with a higher precision are obtained.

Then the comparing circuitry 305 compares the transformed masks (M2, M3, . . . , Mn) with the original masks (M2i, M3i, . . . , Mni) extracted from the lung region, taking the similarity between two masks at individual time phases, i.e., J in the above equation (1), as the comparison result (step S305), and, when J is no less than the threshold (which is "YES" in step S306), the similarity is considered to be acceptable; at the moment, the transformed masks are merged with the original masks extracted directly from the lung region by the transforming circuitry 304 to generate new masks (M2n, M3n, . . . , Mnn), the original masks extracted directly from the lung region are replaced by the new masks (step S308). More specifically, when the similarity is no less than the threshold, the transforming circuitry 304 further generates merged line structures by merging the estimated line structures and the temporary line structures together, and takes the merged structure as the line structures at other time phases.

When J is less than the threshold (which is "NO" in step S306), the similarity is considered to be unacceptable; at the moment, a local rigid registration is performed by the calculating circuitry 303 between the specified branch of the transformed masks (M2, M3, . . . , Mn) and the specified branch of the original masks (M2i, M3i, . . . , Mni) extracted from the lung region to calculate the motion amount. More specifically, when the similarity is less than the threshold, the calculating circuitry 303 performs a local rigid registration between the specified branches of the bronchus in the lung field and then recalculates the motion amount. Thereafter, the transforming circuitry 304 further transforms the transformed masks (M2, M3, . . . , Mn) based on the motion amounts. More specifically, the transforming circuitry 304 further transforms the estimated line structures based on the recalculated motion amount. The comparing circuitry 305 then compares the re-transformed masks with the original masks extracted directly from the lung region (step S307), and the local rigid registration based on the calculating circuitry 303 and the re-transformation on the transformed masks based on the transforming circuitry 304 are repeated until the comparison result by the comparing circuitry 305 becomes no less than the threshold. In other words, the comparing circuitry 305 calculates the similarity by comparing again the re-transformed estimated line structures and the temporary line structures, and repeatedly causes the calculating circuitry 303 and the transforming circuitry 304 to perform processing thereof until the calculated similarity becomes no less than the threshold.

The specified branches can both be specified by the operator in accordance with the degree of deviation on the branches of the two masks displayed on the display, and be specified by the computer automatically identifying the degree of deviation on the branches of the two masks.

According to the above processing course, in the case of an unacceptable registration precision, the present embodiment repeats the registration until the registration precision is acceptable, so as that an improved registration precision can be provided.

Moreover, the present embodiment preferably merges the masks at the inspiration time phase with the masks at the expiration time phase to generate new masks. In this case, the errors resulting from the missing in the extraction course of a certain respiration stage, such as the missing in the line structure extracted at the inspiration time phase or in the line structure extracted at the expiration time phase, can be eliminated, a more completed line structure of the branches of the airway can be obtained.

Figure 10A:
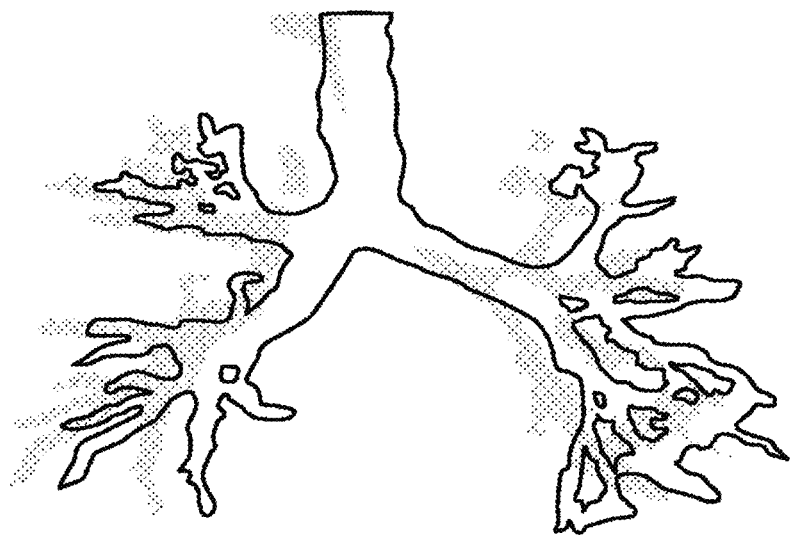
FIG. 10A represents a pair of masks in overlapping state before being merged.

FIG. 10A represents a pair of masks in overlapping state before being merged. The dark part in FIG. 10A represents the mask at the expiration time phase obtained by transforming the mask at the inspiration time phase, and the light part in FIG. 10A represents the original mask extracted directly at the same expiration time phase. As it can be seen from FIG. 10A, the branches of the mask at the expiration time phase gained by transforming the mask at the inspiration time phase are more completed than the branches of the mask extracted directly at the same time phase.

Figure 10B:
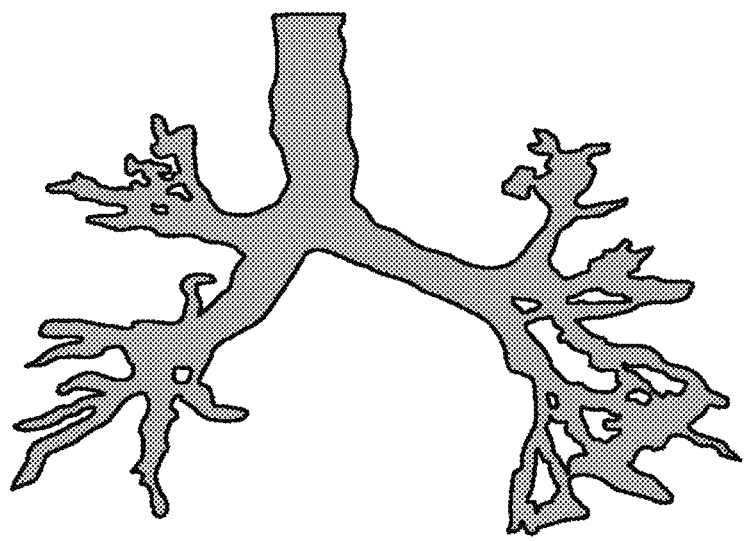
FIG. 10B represents the morphology of a pair of masks in overlapping state after being merged.

FIG. 10B shows the morphology of a pair of masks in overlapping state after being merged.

Moreover, it is preferable in the present embodiment that: after replacing the original masks M2$i$, M3$i$, . . . , Mn$i$ extracted from the lung region with the new masks M2$n$, M3$n$, . . . , Mn$n$ (step S308), the new central lines C2$n$, C3$n$, . . . , Cn$n$ of the airway extracted from the new masks M2$n$, M3$n$, . . . , Mn$n$ serve as the central lines of the airway at other individual time phases P2, P3, . . . , Pn respectively, and afterwards, labels are assigned to the branches of the new central lines C2$n$, C3$n$, . . . , Cn$n$ of the airway, matching them with the labeled central lines of the airway at the benchmark time phase P1, obtaining the matching result representing the matching degree of the both (step S309).

Figure 11A:
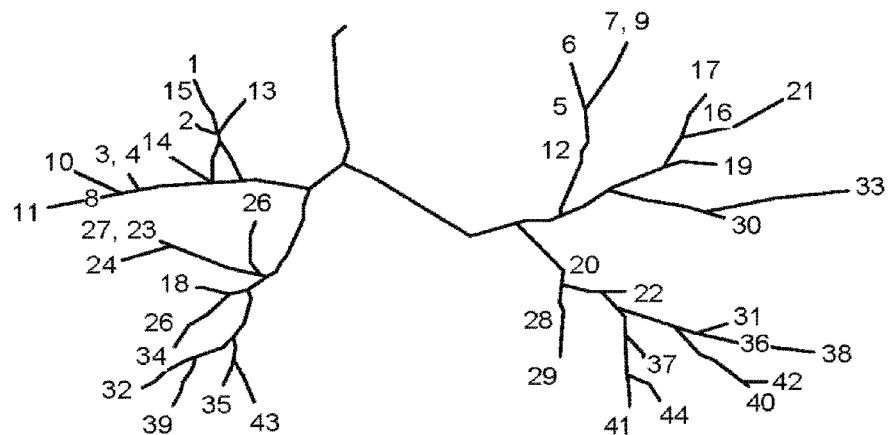
FIG. 11A is a central line tree with a matching label extracted after taking the transformation of embodiment 3 at an inspiration time phase.
Figure 11B:
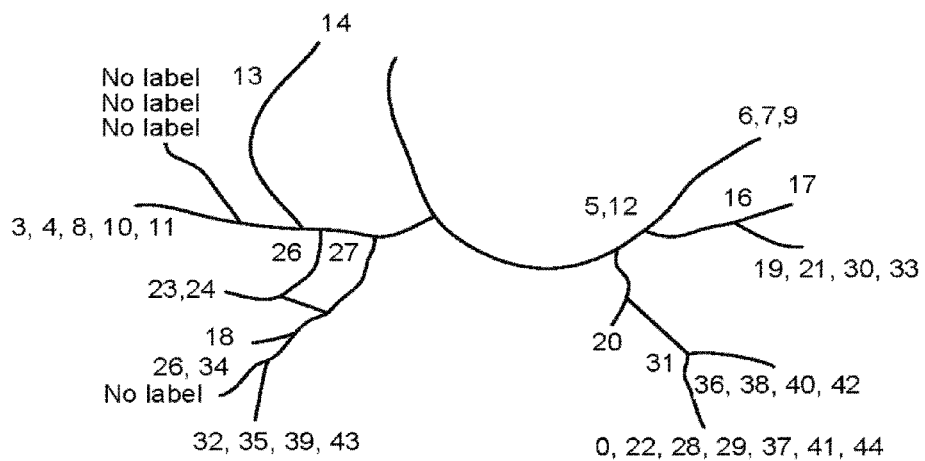
FIG. 11B is a central line tree with a matching label directly extracted at an expiration time phase.

FIG. 11A and FIG. 11B are diagrams used as contrasting examples representing the situation of the central line matching between the central line trees extracted after taking the transformation of the present embodiment and the central line tree directly extracted. FIG. 11A is a central line tree with a matching label extracted after performing the transformation of the present embodiment at an inspiration time phase. FIG. 11B is a central line tree with a matching label directly extracted at an expiration time phase. At the moment, the matching result of the central lines of FIG. 11B and FIG. 11A is 80%; the parts marked with a circle in FIG. 11B are the parts having differences from the central line tree with matching labels at the certain inspiration time phase. It can be seen from the comparison of FIG. 11B and FIG. 11A that comparing the central line tree extracted after the transformation of the present embodiment at a time phase with the central line tree extracted directly at other time phases, the airway branches obtained by the former are more completed than that of the latter, since the latter has missing on some airway branches, the central line matching for the both is only 80%.

Then, in accordance with the method shown in the present embodiment, the mask at the benchmark time phase is transformed into the mask at expiration time phase shown in FIG. 11B, the central line tree at the expiration time phase is extracted, and a local rigid registration to the specified branch is performed; after the local rigid registration, the central line matching for FIG. 11A and FIG. 11B is re-performed. The result of the central line matching now is approximately 100% due to the good registration precision.

According to the results of thus twice performing central line matching, it can be known that a more completed line structure of the airway branches can be gained by the present embodiment. Furthermore, if the central lines of the airway are used to replace the masks in the present embodiment, i.e. the central lines of the airway at the benchmark time phase and other individual time phases are obtained by the obtaining circuitry 302 in step S302, then labels are only assigned to the branches of the new central lines C2$n$, C3$n$, . . . , Cn$n$ of the airway in step S309, matching them with the labeled central lines of the airway at the benchmark time phase P1, obtaining the matching result representing the matching degree of the both without the step of extracting the central line.

Embodiment 4

Figure 12:
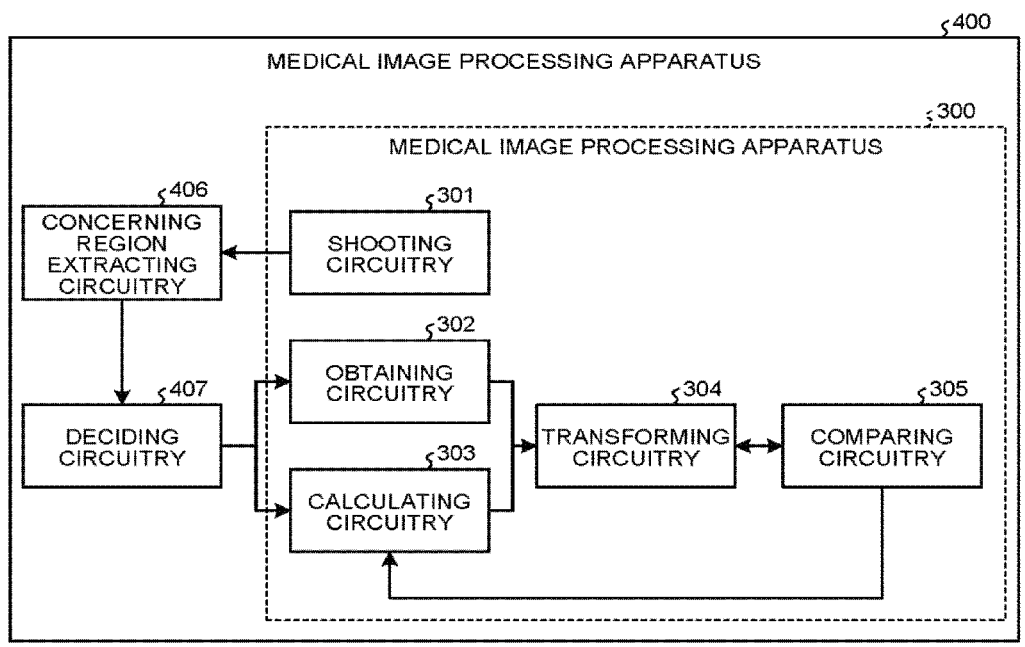
FIG. 12 is a block diagram representing a medical image processing apparatus of embodiment 4.

FIG. 12 is a block diagram representing the medical image processing apparatus of embodiment 4.

As shown in FIG. 12, besides the shooting circuitry 301, the obtaining circuitry 302, the calculating circuitry 303, the transforming circuitry 304 and the comparing circuitry 305 in the medical image processing apparatus 300, a medical image processing apparatus 400 in embodiment 4 further comprises: concerning region extracting circuitry 406 and deciding circuitry 407. Wherein the concerning region extracting circuitry 406 is not essential and can be omitted. The element with like reference numbers represents the same as that in embodiment 3. Only the differences are illustrated below, with the description on the same parts omitted.

The concerning region extracting circuitry 406 extracts the region of interest by the observer (e.g., the lung region) from the components in the medical images taken by the shooting circuitry 301, and takes the extracted region as the concerning region. The concerning region can be the pre-scribed region both specified by the operator manually and gained based on the calculation of a computer.

The deciding circuitry 407 decides a time phase from the plurality of time phases on the time sequence for shooting the subject as the benchmark time phase. In accordance with the benchmark time phase P1 decided by the deciding circuitry 407, the obtaining circuitry 302 obtains the central line C1 of the trachea and bronchus of the tree-like line structure from the lung region at the benchmark time phase P1 as the benchmark line structure, to perform the subsequent transformation from the central line C1 at the benchmark time phase P1 to the central line (C2, C3, . . . , Cn) at other individual time phases (P2, P3, . . . , Pn).

With respect to the deciding method of the benchmark time phase, it can be decided based on the dimension of the extracted concerning region, and it can also be decided based on the pixel values of the concerning region; it is also operable to calculate the mean density of the concerning region in accordance with the pixel values of the concerning region first and then decided the benchmark time phase according to the calculated mean density. In the embodiment, the time phase used as the benchmark time phase can be decided based on the dimension of the lung region; the time phase used as the benchmark time phase can also be decided based on the pixel values of the lung region; it is also operable to calculate the mean density of the lung in accordance with the pixel values of the lung region first, then decide the benchmark time phase in accordance with the calculated mean density of the lung.

The processing procedure of the medical image processing apparatus 400 of the present embodiment then is illustrated in the following. FIG. 13 is a flowchart representing the processing procedure of the medical image processing apparatus of embodiment 4.

The medical image processing apparatus 400 takes medical images of a subject at a plurality of time phases by the shooting circuitry 301 (step S401). Then the concerning region extracting circuitry 406 extracts the lung region used as the concerning region from the medical images (step S402). Then the deciding circuitry 407 decides the benchmark time phase P1 based on the parameters of the lung region (step S403), the parameters of the lung region mentioned herein refer to at least one of the dimension of the lung region, the pixel values of the lung region and the mean density of the lung region.

In the present embodiment, the maximal inspiration time phase or the maximal expiration time phase is decided as the benchmark time phase. The maximal inspiration time phase is the time phase in the inspiration stage where the trachea width is maximal; and the maximal expiration time phase is the time phase in the expiration stage where the trachea width is maximal.

The reason for deciding the maximal inspiration time phase or the expiration time phase as the benchmark time phase is the same as that for embodiment 2, therefore the description is omitted.

By deciding the maximal inspiration time phase or the maximal expiration time phase as the benchmark time phase, the present embodiment can have all the branches of the airway including the tiny local regions completely extracted and obtain a more completed observational image of the airway with a higher reliability.

The subsequent steps of the present embodiment is the same as those of embodiment 3, therefore the description is omitted. More specifically, processing in step S404 to step S411 corresponds to the processing in step S302 to S309 illustrated in FIG. 9.

According to the structures described in the above embodiments 1 to 4, the following effects can be achieved.

According to the medical image processing apparatus involved by the embodiments, with the line structure C1 at the benchmark time phase P1 obtained by the obtaining circuitry and the motion vectors V2, V3, ..., Vn of the components in the lung region from the benchmark time phase P1 to other individual time phases P2, P3, ..., Pn calculated by the calculating circuitry, the transforming circuitry transforms the central line C1 into the line structures C2, C3, ..., Cn at other individual time phases, respectively.

The transformed central lines C2, C3, ..., Cn are the line structures which have the positional movement of the airway produced as the movement of the lung region removed and only represent the movement of the airway itself, so as that the changes of the airway itself can be detected precisely.

Moreover, according to the medical image processing apparatus involved by the embodiments, the deciding circuitry decides the benchmark time phase based on at least one of the dimension of the lung region, the pixel values of the lung region and the mean density of the lung region. Preferably, the maximal inspiration time phase or the maximal expiration time phase is decides as the benchmark time phase.

Thereby the embodiment can have all the branches of the airway including the tiny local regions completely extracted and obtain a more completed observational image of the airway with a higher reliability.

Moreover, according to the medical image processing apparatus involved by the embodiments, the obtaining circuitry obtains not only the line structure M1 of the trachea and bronchus at the benchmark time phase P1, but also the line structures (M2$i$, M3$i$, ..., Mn$i$) of the trachea and bronchus at other individual time phases (P2, P3, ..., Pn) as the temporary line structures. The transforming circuitry transforms the line structure M1 into the line structures (M2, M3, ..., Mn) at other individual time phases respectively with the line structure M1 and the motion vectors (V2, V3, ..., Vn); comparing the transformed line structure (M2, M3, ..., Mn) with the temporary line structures (M2$i$, M3$i$, ..., Mn$i$), if the comparison result is no less than the threshold, the two line structures are merged to generate a new line structure, and if the comparison result is less than the threshold, the local rigid registration and the re-transformation are repeated on the specified branches of the transformed line structures, until the comparison result becomes no less than the threshold.

Thereby, the embodiment can improve the registration precision, which in turn can have all the branches of the airway including the tiny partial regions completely extracted, and obtain a more completed observational image of the airway with a higher reliability.

Moreover, according to the medical image processing apparatus involved by the embodiments, by matching the new central line of the line structure with the central line at the benchmark time phase after the line structures being merged, the precision of the registration process can be verified, so as to guarantee that a more completed line structure of the airway branches can be obtained.

OTHER EMBODIMENTS

Embodiments are not limited to the above embodiments.

In the above embodiments, a case is described where the comparing circuitry 305 further compares the estimated line structures and the temporary line structures to calculate the similarity. However, embodiments are not limited to this case. For example, the comparing circuitry 305 may determine whether the motion amount calculated by the calculating circuitry 303 is no less than a prescribed threshold. Thereafter, when the motion amount is no less than the prescribed threshold, the calculating circuitry 303 performs a rigid registration between the medical image at the benchmark time phase and each of the medical images at other time phases and then recalculates the motion amount. The transforming circuitry 304 obtains an estimated line structure, which is estimated as a line structures at the other time phase by transforming the benchmark line structure based on the motion amount re-calculated by the calculating circuitry 303.

In description of the above embodiments, the illustrated constituent components in the apparatuses are functionally conceptual, and are not necessarily configured physically as illustrated. More specifically, the specific forms of distribution or integration of the apparatuses are not limited to the illustrated forms, and the whole or a part of each of the apparatuses can be configured functionally or physically distributed or integrated in any form of units, depending on various types of loads, usage conditions, and the like. Furthermore, the whole or a part of each of the various processing functions that the apparatuses perform can be implemented by a CPU and a program executed by the CPU, or implemented as hardware by wired logic.

The control method described in the above embodiments can be implemented by executing a previously prepared control program on a computer such as a personal computer or a workstation. This control program can be distributed via a network such as the Internet. This control program can also be recorded on a computer-readable recording medium such as a hard disk, a flexible disk (FD), a compact disc read only memory (CD-ROM), a magnetic optical disc (MO), or a digital versatile disc (DVD) to be executed by being read out from the recording medium by the computer.

According to any one of the above embodiments, the changes in line structure of the bronchus can be precisely reproduced at individual time phases.

In the above, various embodiments of the present invention are described; however, the embodiments described above are for examples only, and are not intended to limit the scope of the present invention. These embodiments can be implemented in a variety of other ways. In addition, without departing from the scope of the substance of the invention, a variety of abbreviations, substitutions and alterations can be done. Various abbreviations, alternations and modifications can be made without departing from the scope of the substance of the present invention. These embodiments and the variations thereof are all encompassed in the scope and the substance of the present invention, and in the scopes of the invention recited in of the claims and the equivalents thereof.

What is claimed is:

1. A medical image processing apparatus, comprising:
   obtaining circuitry configured to take an expiration time phase or an inspiration time phase as a benchmark time phase and obtain a benchmark line structure, which is a line structure of a bronchus in a lung field, from a medical image at the benchmark time phase;
   calculating circuitry configured to calculate a motion amount between a certain component depicted in the medical image at the benchmark time phase and a certain component depicted in a medical image at at least one other time phase than the benchmark time phase; and
   transforming circuitry configured to transform the benchmark line structure based on the motion amount to obtain an estimated line structure, which is estimated as a line structure at the at least one other time phase.

2. The medical image processing apparatus according to claim 1, further comprising deciding circuitry configured to decide the medical image at the benchmark time phase, based on a dimension of the lung field depicted in a medical image.

3. The medical image processing apparatus according to claim 1, further comprising deciding circuitry configured to decide the medical image at the benchmark time phase, based on pixel values of the lung field depicted in a medical image.

4. The medical image processing apparatus according to claim 3, wherein the deciding circuitry calculates a mean lung density based on the pixel values, and decides the medical image at the benchmark time phase.

5. The medical image processing apparatus according to claim 2, wherein the deciding circuitry takes a maximal inspiration time phase or a maximal expiration time phase as the benchmark time phase, and decides the medical image at the benchmark time phase.

6. The medical image processing apparatus according to claim 3, wherein the deciding circuitry takes a maximal inspiration time phase or a maximal expiration time phase as the benchmark time phase, and decides the medical image at the benchmark time phase.

7. The medical image processing apparatus according to claim 1, wherein, when positions of prescribed key points on the estimated line structure is maintained based on the medical image at the at least one other time phase, the transforming circuitry repositions a central line of branches of the estimated line structure to a centers of the bronchus at the at least one other time phase.

8. The medical image processing apparatus according to claim 1, wherein, when positions of prescribed key points on the estimated line structure is maintained, the transforming circuitry smoothes the branches of the estimated line structure with the positions of key points on the estimated line structure maintained.

9. The medical image processing apparatus according to claim 1, further comprising comparing circuitry configured to determine whether the motion amount is no less than a certain threshold, wherein,
   when the motion amount is no less than the certain threshold, the calculating circuitry performs a rigid registration between the medical image at the benchmark time phase and the medical image at the at least one other time phase, and then recalculates the motion amount.

10. The medical image processing apparatus according to claim 9, wherein
    the obtaining circuitry further obtains a line structure of the bronchus in the lung field of the medical image at the at least one other time phase as a temporary line structure,
    the comparing circuitry compares the estimated line structure with the temporary line structure to calculate a similarity, and
    when the similarity is no less than a threshold, the transforming circuitry merges the estimated line structure with the temporary line structure to further generate a merged line structure, and takes the merged line structure as the line structure at the at least one time phase.

11. The medical image processing apparatus according to claim 10, wherein
    when the similarity is less than the threshold, the calculating circuitry performs a local rigid registration on the specified branch of the bronchus in the lung field, and then recalculates a motion amount,
    the transforming circuitry further transforms the estimated line structure based on the recalculated motion amount, and
    the comparing circuitry again compares the further transformed estimated line structure with the temporary line structure to calculate a similarity, and
    repeatedly causes the calculating circuitry and the transforming circuitry to perform processing thereof until the calculated similarity becomes no less than the threshold.

12. The medical image processing apparatus according to claim 1, wherein the calculating circuitry calculates the motion amount by performing a registration between the medical image at the benchmark time phase and the medical image at the at least one other time phase.

13. The medical image processing apparatus according to claim 1, wherein the transforming circuitry transforms the benchmark line structure into the estimated line structure by assigning the benchmark line structure the motion amount corresponding thereto.

14. The medical image processing apparatus according to claim 1, wherein the obtaining circuitry obtains a reference line of the bronchus in the lung field as the line structure.

15. The medical image processing apparatus according to claim 1, wherein the obtaining circuitry obtains a region corresponding to the bronchus in the lung field as the line structure.

16. The medical image processing apparatus according to claim 1, wherein the medical images are three-dimensional (3D) medical images.

17. The medical image processing apparatus according to claim 1, further comprising:
  concerning region extracting circuitry configured to extract images of the lung field as images of a concerning region from a medical images; and
  deciding circuitry configured to decide the medical image at the benchmark time phase, based on the concerning region depicted in the medical images.

18. A medical image processing method comprising:

taking an expiration time phase or an inspiration time phase as a benchmark time phase and obtaining a benchmark line structure, which is a line structure of a bronchus in a lung field, from a medical image at the benchmark time phase;

calculating a motion amount between a certain component depicted in the medical image at the benchmark time phase and a certain component in a medical image at at least one other time phase than the benchmark time phase; and transforming the benchmark line structure based on the motion amount to obtain an estimated line structure, which is estimated as a line structure at the at least one other time phase.

* * * * *